(12) United States Patent
Ferguson

(10) Patent No.: US 11,207,062 B2
(45) Date of Patent: Dec. 28, 2021

(54) SUTURE AND SOFT ANCHOR ASSEMBLY AND METHOD OF MAKING THE SAME

(71) Applicant: RIVERPOINT MEDICAL, LLC, Portland, OR (US)

(72) Inventor: Patrick Edward Ferguson, Portland, OR (US)

(73) Assignee: RIVERPOINT MEDICAL, LLC, Portland, OR (US)

( * ) Notice: Subject to any disclaimer, the term of this patent is extended or adjusted under 35 U.S.C. 154(b) by 6 days.

(21) Appl. No.: 16/703,921

(22) Filed: Dec. 5, 2019

(65) Prior Publication Data

US 2020/0107828 A1   Apr. 9, 2020

Related U.S. Application Data

(63) Continuation of application No. 15/345,950, filed on Nov. 8, 2016, now Pat. No. 10,531,871, which is a continuation-in-part of application No. 14/081,112, filed on Nov. 15, 2013, now Pat. No. 9,486,202.

(51) Int. Cl.
*A61B 17/04* (2006.01)
*A61B 17/00* (2006.01)

(52) U.S. Cl.
CPC ...... *A61B 17/0401* (2013.01); *A61B 17/0485* (2013.01); *A61B 2017/00526* (2013.01); *A61B 2017/0404* (2013.01); *A61B 2017/0406* (2013.01); *A61B 2017/0458* (2013.01); *A61B 2017/0464* (2013.01); *Y10T 29/49838* (2015.01)

(58) Field of Classification Search
CPC .......... Y10T 29/49838; A61B 17/0401; A61B 17/0485; A61B 2017/0404; A61B 2017/0464; A61B 2017/0406; A61B 2017/00526; A61B 2017/0458; A61B 17/0642; A61F 2/0811
See application file for complete search history.

(56) References Cited

U.S. PATENT DOCUMENTS 6,296,659 B1   10/2001   Foerster
7,959,650 B2    6/2011   Kaiser et al.
8,088,130 B2    1/2012   Kaiser et al.
(Continued)

FOREIGN PATENT DOCUMENTS

RU   2012272 C1   5/1994
RU   2190974 C1   4/1996
RU   2112434 C1   6/1998

*Primary Examiner* — Lawrence Averick
(74) *Attorney, Agent, or Firm* — Timothy E. Siegel Patent Law, PLLC; Timothy E. Siegel

(57) ABSTRACT

A method of anchoring a suture into a pilot hole in bone utilizing a suture anchor. A lumen-defining circular soft wall, having a first and second end, is slidably engaged to a piece of suture, a first length of which extends from the first end of the wall and is threaded through the lumen from the second end, and a second length of which extends from the second end and is threaded through the lumen from the first end. The suture anchor is introduced into the pilot hole so that the first length and second length of suture material extend out of the pilot hole. The first length and second length are pulled on alternately, thereby permitting the suture anchor structure to slide on the piece of suture material, and to be compacted evenly by the pulling, until the suture anchor is set in the pilot hole.

7 Claims, 4 Drawing Sheets

(56) References Cited

U.S. PATENT DOCUMENTS

| | | | |
|---|---|---|---|
| 8,231,654 B2 | 7/2012 | Kaiser et al. | |
| 8,298,284 B2 | 10/2012 | Cassani | |
| 9,486,202 B2 | 11/2016 | Ferguson | |
| 10,070,856 B1 * | 9/2018 | Black et al. | |
| 10,070,865 B2 * | 9/2018 | Scirica | A61B 17/068 |
| 10,531,871 B2 | 1/2020 | Ferguson | |
| 2002/0111653 A1 | 8/2002 | Foerster | |
| 2004/0267313 A1 | 12/2004 | Amery et al. | |
| 2005/0118716 A1 | 6/2005 | Howland | |
| 2009/0318961 A1 | 12/2009 | Stone et al. | |
| 2010/0016892 A1 | 1/2010 | Kaiser et al. | |
| 2011/0098727 A1 | 4/2011 | Kaiser et al. | |
| 2013/0066423 A1 | 3/2013 | Bishop | |
| 2013/0096612 A1 | 4/2013 | Zajac et al. | |
| 2013/0110165 A1 | 5/2013 | Burkhart et al. | |
| 2013/0296934 A1 | 11/2013 | Sengun | |
| 2018/0338756 A1 * | 11/2018 | Black | A61B 17/0401 |

* cited by examiner

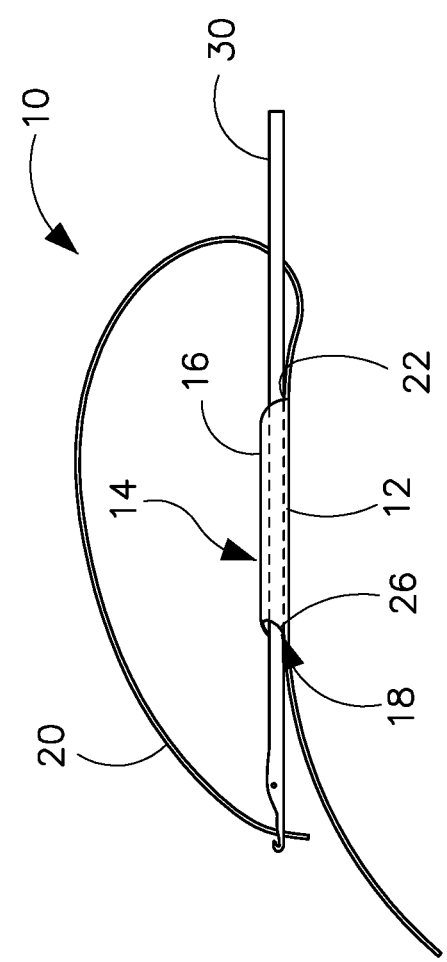
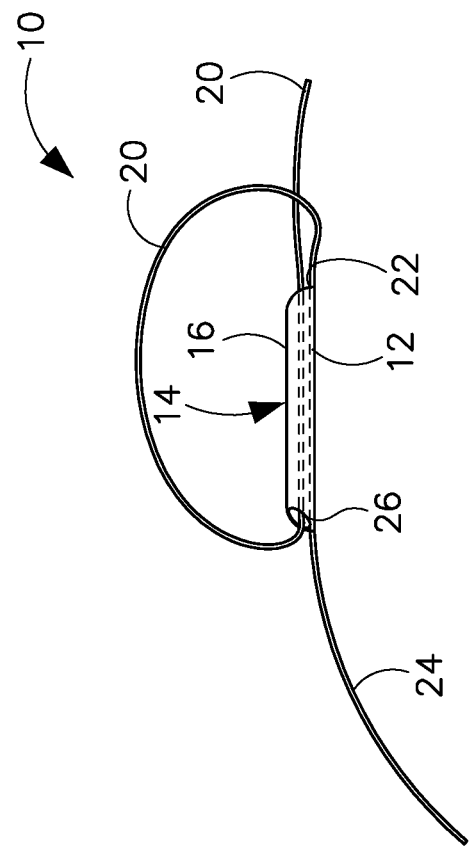
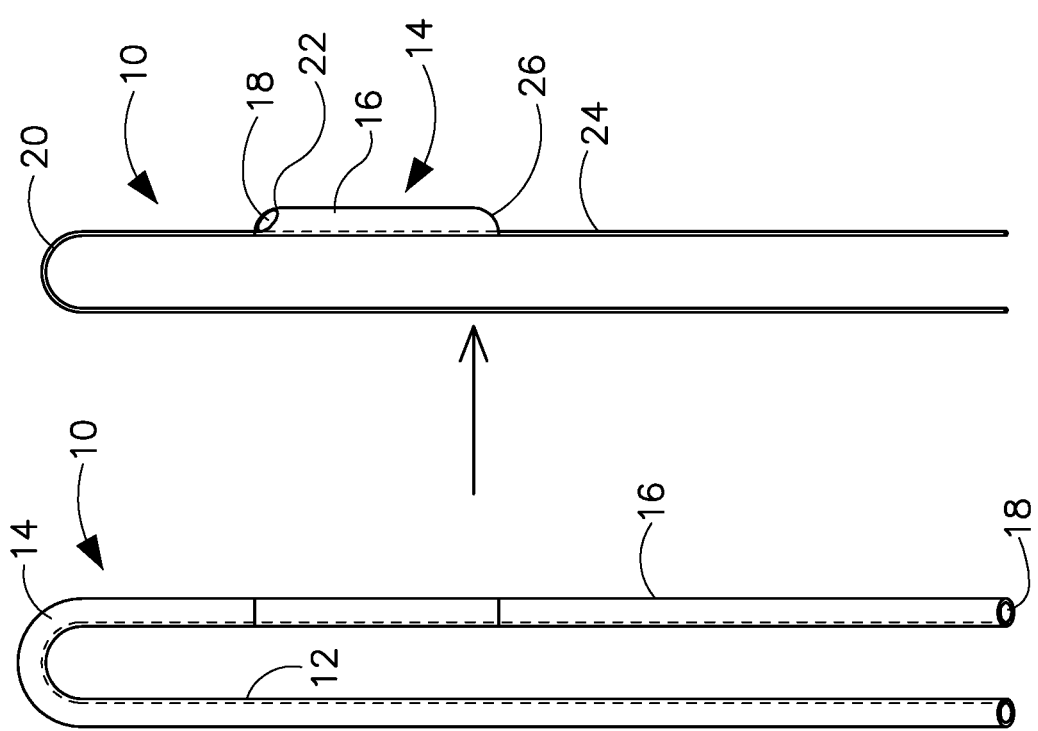
FIG. 1
FIG. 2
FIG. 3
FIG. 4

SUTURE AND SOFT ANCHOR ASSEMBLY AND METHOD OF MAKING THE SAME

RELATED APPLICATION

This application is a continuation of application Ser. No. 15/345,950, filed Nov. 8, 2016, which itself is a continuation-in-part of application Ser. No. 14/081,112, filed Nov. 15, 2013, now U.S. Pat. No. 9,486,202 issued Nov. 8, 2016, both of which are hereby incorporated by reference as if fully set forth herein.

BACKGROUND

In performing various surgical repair operations, it is necessary to anchor a suture to bone, typically in order to connect muscle to the bone, in the same manner as a healthy tendon. One apparatus for effecting this anchoring is to provide a suture that has some structure on or about it that can be compacted by a surgeon performing some action, such as drawing on a piece of suture material. The structure is introduced into a pilot hole, and is compacted, so that it forms a hard ball that sets by digging into the sides of the pilot hole, thereby anchoring the suture.

Although the soft suture anchor has a range of advantages over metal anchors, such as screws, the setting action is not always as robust as would be desirable. A poorly set anchor may work its way loose over time, resulting in slop in the bone-muscle connection, which could cause a great deal of dissatisfaction on the part of a patient. In the worst case situation, the anchor works its way free of the bone, undoing the bone-to-muscle connection.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

In a first separate aspect, the present invention may take the form of a suture assembly, including a soft anchor made up of a piece of suture material and a soft structure, of greater diameter and a shorter length than the piece of suture material and having a circular soft wall, defining an interior lumen and having a first end and a second end opposed to the first end. The first piece of suture material extends longitudinally through the circular soft wall in such a manner that the soft structure can slide along the piece of suture material and thereby defines a first length of the piece of suture material, extending from engagement with the circular soft wall at the first end and a second length of the piece of suture material, extending from engagement with the circular soft wall at the second end. Finally, the first length is threaded through the lumen, entering at the second end and the second length is threaded through the lumen, entering at the first end. Accordingly, an anchor is formed, made up of said circular soft wall with said lengths looped about it, and said lengths extend outward, available for attachment to anatomical structures.

In a second separate aspect, the present invention may take the form of a method of anchoring a suture into a pilot hole in bone. The method utilizes a suture anchor structure, wherein a lumen-defining circular soft wall, having a longitudinal first end and an opposed second end, is slidably engaged to a piece of suture material, and wherein a first length of the suture material extends from the first end of the wall and is threaded through the lumen from the second end, and a second length of the suture material extends from the second end and is threaded through the lumen from the first end. The suture anchor structure is introduced into the pilot hole so that the first length and second length of suture material extend out of the pilot hole. The first length and second length are pulled on alternately, thereby permitting the suture anchor structure to slide on the piece of suture material, and to be compacted evenly by the pulling, until the suture anchor is set in the pilot hole.

In a third separate aspect, the present invention may take the form of a method of making a suture assembly, including a soft suture anchor, that utilizes a piece of suture material and includes the step of constructing a soft structure about the piece of suture material, such that the soft structure is slidably engaged to the piece of suture material, and wherein the soft structure defines a lumen, separate from the slidable engagement of the soft structure to the piece of suture. Further, the soft structure has a first longitudinal end out of which extends a first length of the piece of suture material and has a second longitudinal end opposed to the first longitudinal, out of which extends a second length of the piece of suture material. The first length is threaded through the lumen from the second to the first end, such that the first length extends out of the lumen at the first end of the soft structure and the second length is threaded through the lumen, from the first end to the second such that the second length extends out of the lumen at the second end of the soft structure. The soft structure and the portions of the lengths that are looped about it form a soft anchor, and the portion of the lengths extending outwardly from the lumens are available for attachment to anatomical features.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced drawings. It is intended that the embodiments and figures disclosed herein are to be considered illustrative rather than restrictive.

FIG. 1 is a side isometric view of a workpiece representing a step in the production of a suture and soft anchor assembly, according to the present invention.

FIG. 2 is a side isometric view of the workpiece of FIG. 1 at a further stage in the production process, wherein a soft structure having a lumen and a pair of suture lengths extending therefrom have been defined.

FIG. 3 is a side isometric view of the workpiece of FIG. 2 at a further stage of the production process, wherein a first suture length is in the process of being pulled through the lumen.

FIG. 4 is a side isometric view of the workpiece of FIG. 3 at a further stage in the production process, wherein the first suture length has been pulled through the lumen.

DETAILED DESCRIPTION OF THE PREFERRED EMBODIMENTS

Figure 5:
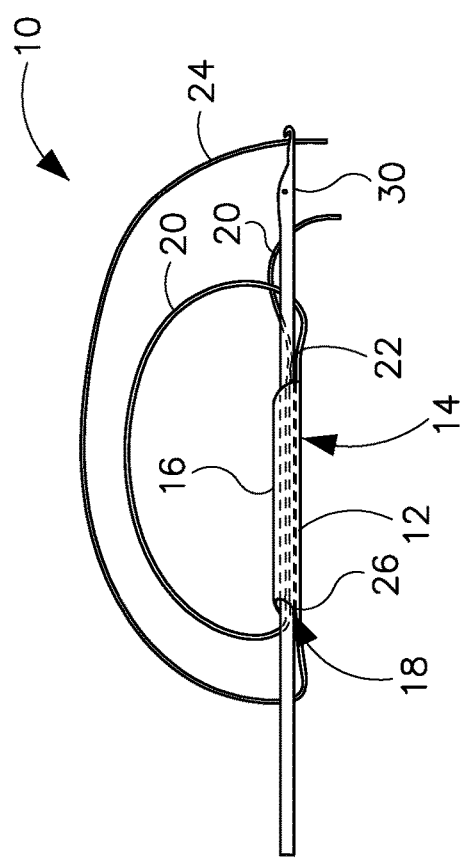
FIG. 5 is a side isometric view of the workpiece of FIG. 4 at a further stage of the production process, wherein the second suture length is in the process of being pulled through the lumen.

Referring to FIGS. 1 and 2, in one preferred embodiment, construction of a suture and anchor assembly begins with a workpiece 10 that is formed by feeding a size 2 suture together with a set of thinner UHWMPE fibers (for example smaller diameter suture material, such as 4-0 suture material) into a suture braiding machine in such a manner that the size 2 piece of suture 12 becomes one of the warp ends (longitudinally running elements) of the resultant workpiece 10. Suture piece 12, together with the remainder of the braid 14 (not including suture piece 12), form a soft structure in the form of a circular wall 16 defining a lumen 18. Workpiece 10 is formed when the product of the braiding machine is cut into a piece that can range in length, depending on the specific application. Then, the remainder of braid 14 is cut on both ends with a cauterizing blade or scissors, so that the remainder of braid 14 now forms a soft structure, as shown in FIG. 2, including a circular wall 16, defining a lumen 18, that only extends along, and is slidingly engaged to, a portion of suture piece 12. As a result, a first length 20 of suture piece 12 extends from a first end 22 of soft structure 16 and a second end 24 extends from a second end 26 of soft structure 16.

Referring to FIGS. 3 through 6, a lacing tool 30 is then used to pull the first length 20 through lumen 18, entering at the second end 26, and thereby forming a loop as shown, and exiting at the first end 22. Then, lacing tool 30 is used to pull the second length 24 through lumen 18, entering at the first end 22, and therefore forming an additional loop as shown, and exiting at the second end 26. The first length 20 extends at least 10 cm from said lumen at said soft structure first end and said second length 24 extends at least 10 cm from said lumen at said soft structure second end.

Figure 7:
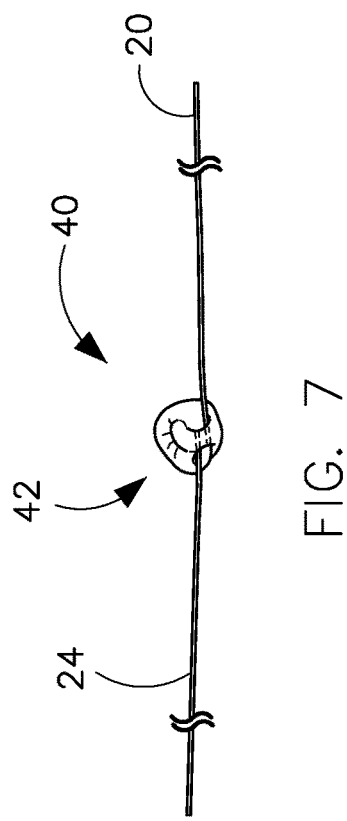
FIG. 7 is a side isometric view of the assembly of FIG. 6, wherein the two suture lengths have been pulled, thereby collapsing and compacting the anchor.
Figure 6:
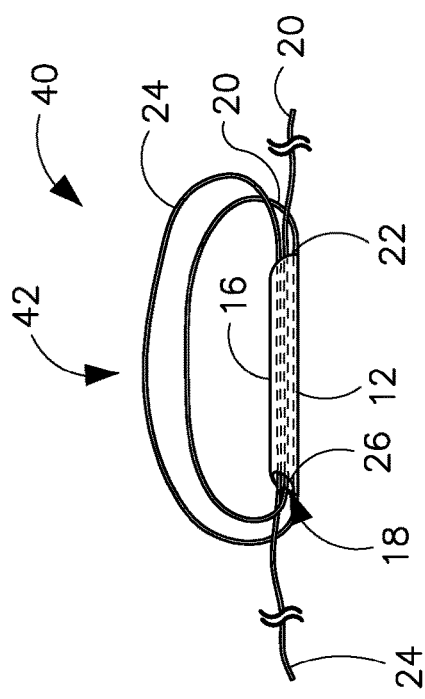
FIG. 6 is a side isometric view of the workpiece of FIG. 5 at a further stage of the production process, wherein the second suture length has been pulled through the lumen, completing assembly having a soft anchor and suture lengths.

Workpiece 10 has now become a finished suture and soft anchor assembly 40, having a soft anchor 42, made up of the circular wall 16 and loops formed by a portion of first length 20 and second length 24. Also, first length 20 and second length 24 extend outwardly for deploying anchor 42 and also for attachment to anatomical structures. Referring to FIG. 7, when first length 20 and second length 24 are pulled, anchor 42 knots up, thereby forming a relatively hard, compacted knot.

Figure 9:
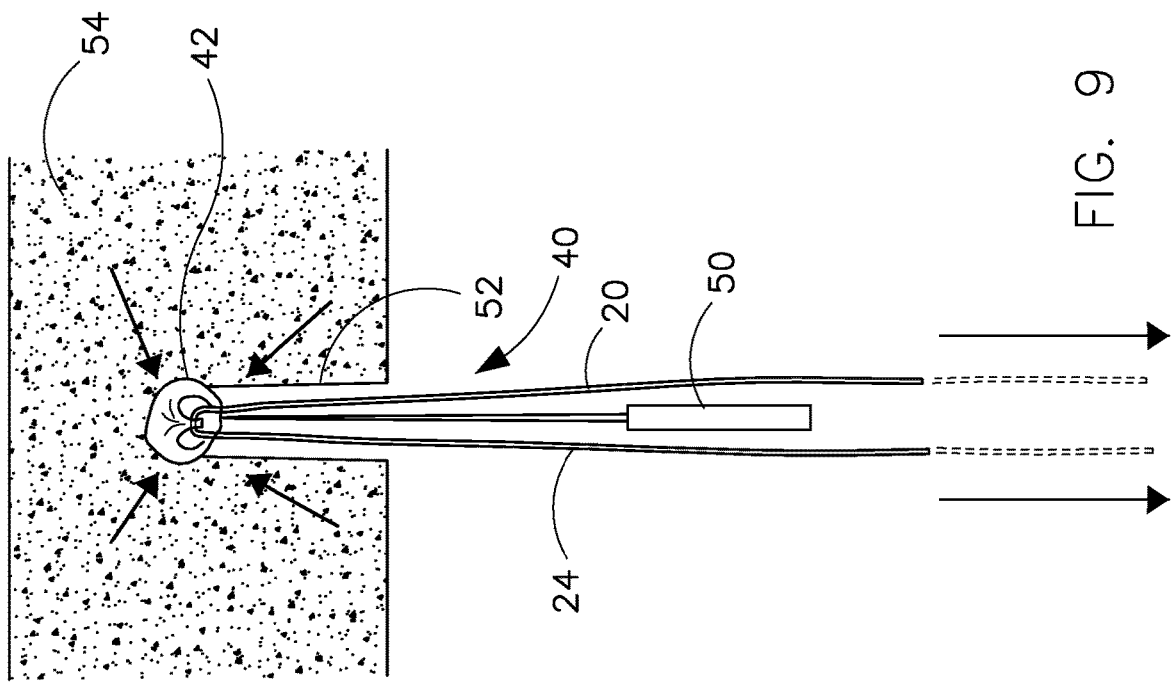
FIG. 9 is a sectional view of a pilot hole in bone showing the assembly of FIG. 6, and wherein the anchor has been deployed by pulling on the lengths.
Figure 8:
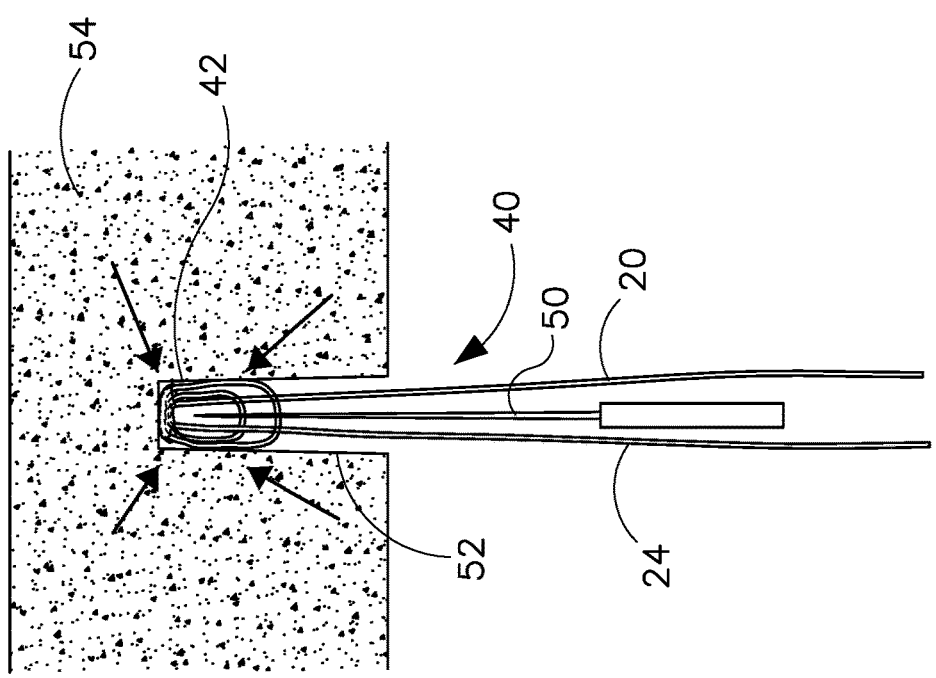
FIG. 8 is a sectional view of a pilot hole in bone showing the assembly of FIG. 6 inserted using an insertion tool.

FIGS. 8 and 9 show the use of assembly 40 with an insertion tool 50 used to place anchor 42 into a pilot hole 52 that has been drilled into bone 54. While tool 50 is being used to retain anchor 42 in stationary position in hole 52, length 20 and 24 are pulled in alternating order. This causes anchor 42 to form a hard knot, digging into bone 54, thereby setting anchor 42 into bone 54 and providing lengths 20 and 24 to be used to retain muscle or to connect to whatever internal structure is desired.

Figures 10, 11:
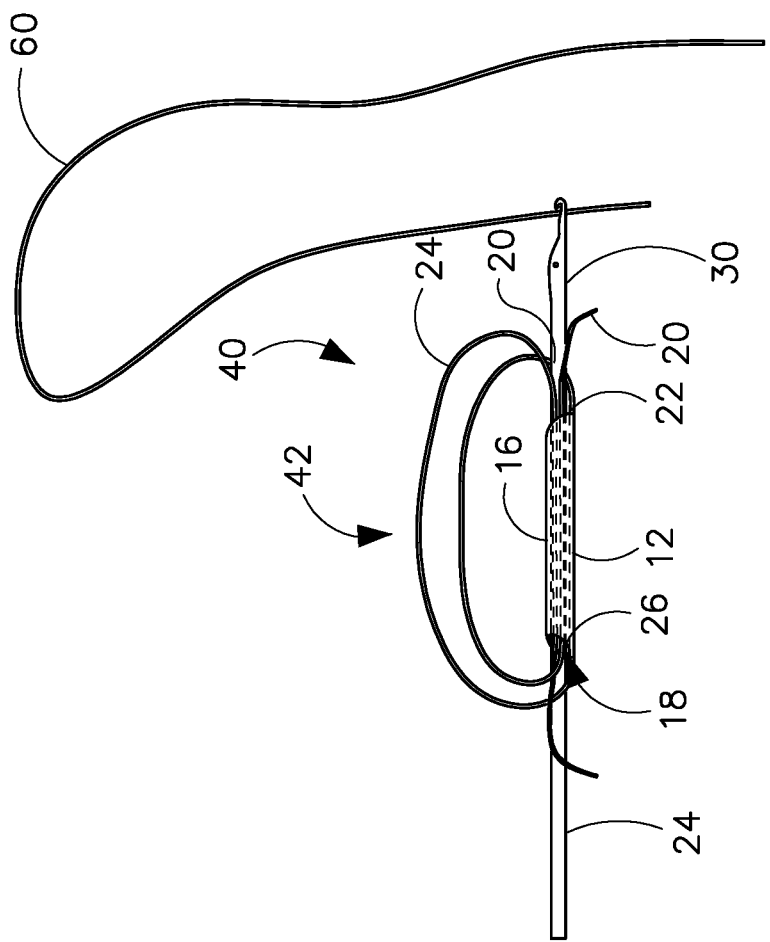
FIG. 10 is a side isometric view of the production of an alternative embodiment, showing the assembly of FIG. 6, and also showing an additional piece of suture in the process of being threaded through the lumen.
FIG. 11 is a side isometric view of a finished alternative embodiment of a suture and soft anchor assembly having four lengths of suture extending from the soft anchor.

Referring to FIGS. 10 and 11, in an alternative preferred embodiment an additional piece of suture material 60 is threaded through lumen 18, looped about and rethreaded through, so that it is retained, to provide additional lengths for tying to other structures, such as muscle or bone, within the body. In further embodiments, further pieces of suture material are also threaded through lumen 18, looped about and rethreaded, to provide still more lengths, for forming further suture connections within the body.

While a number of exemplary aspects and embodiments have been discussed above, those possessed of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

The invention claimed is:

1. A method of anchoring a suture into a pilot hole in bone:
    (a) providing a suture anchor structure,
    wherein a circular soft wall defining a lumen,
    having a longitudinal first end and an opposed second end,
    is slidably engaged to a piece of suture material, and
    wherein a first length of said suture material extends from said first end of said wall and is threaded through said lumen from said second end, and
    a second length of said suture material extends from said second end and is threaded through said lumen from said first end;
    (b) introducing said suture anchor structure into said pilot hole so that said first length and second length of suture material extend out of said pilot hole;
    (c) pulling alternately on said first length and second length,
    thereby permitting said suture anchor structure to slide on said piece of suture material, and
    to be compacted evenly by said pulling,
    until said suture anchor is set in said pilot hole
    wherein an additional suture piece is threaded through said lumen, and
    wherein said additional piece has a first end and a second end and wherein during said method said first end is attached to a first anatomical structure and said second end is attached to a second anatomical structure.

2. The method of claim 1, wherein said soft structure wall is a braid of fibers, forming a circular soft wall that defines said lumen, of which said piece of suture material forms a warp end.

3. The method of claim 2, wherein said fibers of said soft structure are at least 90% ultra-high molecular weight polyethylene (UHWMPE).

4. The method of claim 1, wherein said first length extends at least 10 cm from said lumen at said soft wall first end and said second length extends at least 10 cm from said lumen at said soft wall second end.

5. The method of claim 4,
    wherein said first length is attached to a further anatomical structure and said second length is attached to a further anatomical structure.

6. The method of claim 1, wherein said piece of suture material is at least 90% UHWMPE by weight.

7. The method of claim 1,
wherein yet another suture piece is threaded through said lumen and wherein said yet additional piece has a first end and a second end and wherein during in said method said yet additional piece first end is attached to a first anatomical structure and said yet additional piece second end is attached to a second anatomical structure.

\* \* \* \* \*